(12) United States Patent
Stone et al.

(10) Patent No.: US 6,594,511 B2
(45) Date of Patent: Jul. 15, 2003

(54) METHOD AND APPARATUS FOR DETERMINING PHYSIOLOGICAL CHARACTERISTICS

(76) Inventors: Robert T. Stone, 869 Cumberland Dr., Sunnyvale, CA (US) 94087; Alex K. Mills, 7 Old Westbury La., Webster Groves, MO (US) 63119

( * ) Notice: Subject to any disclaimer, the term of this patent is extended or adjusted under 35 U.S.C. 154(b) by 50 days.

(21) Appl. No.: 09/815,827

(22) Filed: Mar. 23, 2001

(65) Prior Publication Data

US 2001/0037059 A1 Nov. 1, 2001

Related U.S. Application Data

(60) Provisional application No. 60/193,143, filed on Mar. 29, 2000.

(51) Int. Cl.$^7$ .................................................. A61B 5/00
(52) U.S. Cl. ........................ 600/324; 600/322; 600/336
(58) Field of Search ................................ 600/322–324, 600/336, 309, 310, 326; 356/39–42

(56) References Cited

U.S. PATENT DOCUMENTS

| | | | |
|---|---|---|---|
| 4,407,290 A | | 10/1983 | Wilber |
| 4,793,360 A | | 12/1988 | Miyawaki et al. |
| 4,911,167 A | * | 3/1990 | Corenman et al. .......... 600/324 |
| 4,934,372 A | | 6/1990 | Corenman et al. |
| 4,960,126 A | * | 10/1990 | Conlon et al. .............. 600/336 |
| 5,490,505 A | | 2/1996 | Diab et al. |
| 5,685,299 A | * | 11/1997 | Diab et al. .................. 600/300 |
| 5,971,930 A | * | 10/1999 | Elghazzawi ................. 600/483 |

* cited by examiner

Primary Examiner—Eric F. Winakur
Assistant Examiner—Matthew J Kremer
(74) Attorney, Agent, or Firm—Francis Law Group

(57) ABSTRACT

A method for determining physiological characteristics comprising the steps of (a) acquiring a first blood oxygen signal from a subject, the blood oxygen signal having an undesirable artifact signal component; (b) acquiring an additional physiological signal having a heart rate component using an acquisition technique that is different and independent from the first acquiring step; (c) processing the first blood oxygen signal and the physiological signal to provide a first waveform having a reduced level of the artifact signal component therein; (d) processing the first waveform and the physiological signal to provide a reference waveform; and (e) processing the reference waveform and the physiological signal to provide a second blood oxygen saturation signal corresponding to the blood oxygen saturation level of said subject.

19 Claims, 6 Drawing Sheets

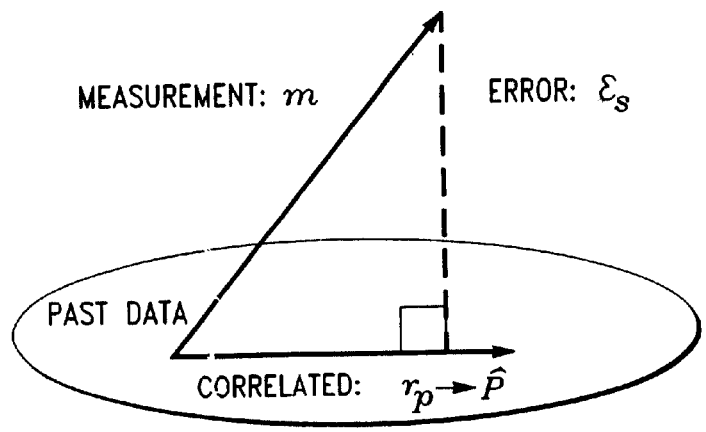
*FIG.—1A*
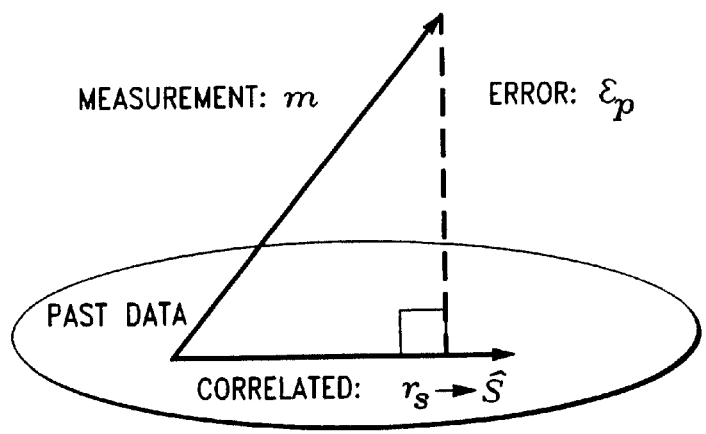
*FIG.—1B*

METHOD AND APPARATUS FOR DETERMINING PHYSIOLOGICAL CHARACTERISTICS

CROSS REFERENCE TO RELATED APPLICATIONS

This application claims benefit under 35 U.S.C. 119 (e) of U.S. Provisional Application No. 60/193,143, filed Mar. 29, 2000.

FIELD OF THE INVENTION

The present invention relates generally to methods for determining physiological characteristics. More specifically, the present invention relates to a method and apparatus for determination of physiological characteristics that employs a plurality of measured physiological signals and an individualized reference signal.

BACKGROUND OF THE INVENTION

Non-invasive photoelectric pulse oximetry for determining blood flow characteristics is well known in the art. Illustrative are the methods and apparatus described in U.S. Pat. Nos. 5,490,505; 4,934,372; 4,407,290; 4,226,554; 4,086,915; 3,998,550; and 3,704,706.

Pulse oximeters typically measure and display various blood flow characteristics including, but not limited, to blood oxygen saturation of hemoglobin in arterial blood, the volume of individual blood pulsations supplying the flesh and the rate of blood pulsations corresponding to each heartbeat of the patient. The oximeters pass light through human or animal body tissue where blood perfuses the tissue such as a finger, an ear, the nasal septum or the scalp, and photoelectrically sense the absorption of light in the tissue. The amount of light absorbed is then used to calculate the amount of blood constituent being measured.

The light passed through the tissue is typically selected to be of one or more wavelengths that is absorbed by the blood in an amount representative of the amount of the blood constituent present in the blood. The amount of transmitted light passed through the tissue will vary in accordance with the changing amount of blood constituent in the tissue and the related light absorption.

The output signal from the pulse oximeter, which is sensitive to the arterial blood flow, contains a component that is waveform representative of the patient's blood gas saturation. This component is referred to as a "plethysmographic wave or waveform" (see FIG. 5).

A problem generally associated with non-invasive pulse oximeters is that the plethysmograph signal (and the optically derived pulse rate) may be subject to irregular variants in the blood flow including, but not limited to, motion artifacts, that interfere with the detection of the blood flow characteristics. A motion artifact is caused by the patient's muscle movement proximate to the oximeter sensor, for example, the patient's finger, ear or other body part to which the oximeter sensor is attached, and may cause spurious pulses that are similar to pulses caused by arterial blood flow. These spurious pulses, in turn, may cause the oximeter to process the artifact waveform and provide erroneous data. This problem is particularly significant with infants, fetuses, or patients that do not remain still during monitoring.

A further problem exists in circumstances where the patient is in poor condition and the pulse strength is very weak. In continuously processing the optical data, it can be difficult to separate the true pulsatile component from artifact pulses and noise because of a low signal to noise ratio. Inability to reliably detect the pulsatile component in the optical signal may result in a lack of the information needed to calculate blood constituents.

Several signal processing methods (and apparatus) have been employed to reduce the effects of the motion artifact(s) on the measured signal(s) and, hence, derived plethysmograph waveform. For example, in U.S. Pat. No. 4,934,372 synchronous averaging (i.e., "C-lock technique") is employed to eliminate the motion artifact(s).

Although the noted method has been embodied in at least one commercially available device, there are several drawbacks associated with the method. Among the drawbacks is that the noise reduction is equal to approximately 1/n, where n equals the number of heartbeats in the synchronous average. The value (n) could thus cause inordinate delays in the determination of blood constituents (e.g., blood saturation).

In U.S. Pat No. 5,490,505 a complex method and apparatus is disclosed that employs a plurality of signal conditioners, a combining network and a correlation canceler to address the "motion artifact" issue. There are several drawbacks associated with the noted method and apparatus.

A major drawback of the '505 method and apparatus is that no noise free reference or signal free noise source is provided to the correlation canceler. The derived plethysmographic waveform may thus not be representative of the patient's true plethysmographic waveform.

The noted method is further based on the questionable assumption that the maximum correlation value ($\omega$) provided by the combining network at the highest saturation is the arterial saturation and the maximum correlation value at the lowest saturation is the venous saturation. It is, however, well known in the art that there are a number of conditions, especially unhealthy conditions, where the motion artifacts will produce a saturation value that is higher than the arterial saturation. Indeed, a pure motion artifact with no blood in the path at all will produce a blood saturation of approximately 81%.

It is therefore an object of the present invention to provide an improved method and apparatus for determining physiological characteristics of a subject and, in particular, the blood oxygen saturation level in the subject's blood.

It is another object of the invention to provide a method and apparatus for determining physiological characteristics of a subject that provides an accurate representation of the subject's plethysmographic waveform.

SUMMARY OF THE INVENTION

In accordance with the above objects and those that will be mentioned and will become apparent below, the method for determining physiological characteristics and, in particular, the blood oxygen saturation level of a subject in accordance with this invention comprises (a) acquiring a first blood oxygen signal from the subject, the blood oxygen signal having an undesirable artifact signal component; (b) acquiring an additional physiological signal having a heart rate component using an acquisition technique that is different and independent from the first acquiring step; (c) processing the first blood oxygen signal and the physiological signal to provide a first waveform having a reduced level of the artifact signal component therein; (d) processing the first waveform and the physiological signal to provide a reference waveform; and (e) processing the reference waveform and the physiological signal to provide a second blood oxygen signal corresponding to the blood oxygen saturation level of said subject.

The apparatus for determining the blood oxygen saturation level of a subject in accordance with the invention comprises an oximeter sensor arrangement coupled to the subject for acquiring a first blood oxygen signal having an artifact component; an ECG detector coupled to the subject for acquiring an ECG signal having a plurality of first r-wave components substantially corresponding to first r-wave events; first processing means for processing the first blood oxygen signal and the ECG signal to provide a first waveform having a reduced level of the artifact component, the first waveform including a plurality of quasi-stationary heartbeat spaces; second processing means for processing the first waveform and the ECG signal to provide a second waveform having said plurality of quasi-stationary heartbeat spaces and a plurality of second r-wave events substantially corresponding to said first r-wave events; and third processing means for processing the first blood oxygen signal and the second waveform to provide a second blood oxygen signal substantially corresponding to the blood oxygen saturation level of said subject.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which:

FIGS. 1A and 1B are a schematic illustrations of a conventional noise/correlation canceling technique;

DETAILED DESCRIPTION OF PREFERRED EMBODIMENTS

The present invention substantially reduces or eliminates the drawbacks associated with conventional pulse oximeters and related signal processing techniques. As discussed in detail below, the method (and apparatus) employs a true, "individualized" reference in conjunction with a correlation canceling technique to eliminate motion artifacts and, hence, provide an accurate representation of the patient's plethysmographic waveform.

Noise/correlation canceling is a well recognized signal processing technique that is employed to "separate" measured data into two or more distinct components (i.e., "correlated" and "uncorrelated"). The operation is generally depicted in Eq. 1, where m is the raw measurement composed of a primary component (p) and a secondary component(s).

$$m = p + s \qquad \text{Eq. 1}$$

The optimal canceler thus separates the measurement (m) into a correlated part (i.e., p or s) depending on the nature of the reference signal (r), where (r) can be correlated to either $p$ ($r_p$) or $s$ ($r_s$).

The optimal solution is one that provides the shortest distance between m and its correlated component. This is called an "orthogonal projection", as shown in FIGS. 1A and 1B.

Thus, if we assume that the reference signal is correlated to the primary, then the canceler will produce an estimate of the primary ($\hat{p}$), and remove it from the measurement to provide an output of the secondary, $$\epsilon_s = m - \hat{p} = [p+s] - \hat{p} = [p-\hat{p}] + s \approx s \qquad \text{Eq. 2}$$

The estimate is a function of the reference ($r_p$). Indeed, the purpose of the canceler is to transform $r_p \rightarrow \hat{p}$. If the canceler accomplishes the noted transformation, then $$p = C_p(r_p) \qquad \text{Eq. 3}$$

and as $$p \rightarrow \hat{p},$$

then $$\epsilon_s \approx s,$$

where $C(\cdot)$ is the canceler transformation.

Similarly, if a secondary reference ($r_s$) is used, then the canceler provides an estimate of the secondary (s) instead of the primary $$\epsilon_p = m - \hat{s} = [p+s] - \hat{s} = [s-\hat{s}] + p \approx p \qquad \text{Eq. 4}$$

which occurs when $$\hat{s} = C_s(r_s) \qquad \text{Eq. 5}$$

and as $$\hat{s} \rightarrow s,$$

then $$\epsilon_p \approx p. \qquad \text{Eq. 5}$$

It can thus be seen that "conceptually", in its simplest form, the correlation canceler provides the optimal decomposition of the signal into its constituent parts or components depending on the choice of the reference signal. It is, however, important to note that the reference dictates not only which signal (p or s) is reflected in the canceler's output, but, also the accuracy of the resultant signal (e.g., plethysmographic waveform).

Figure 8:
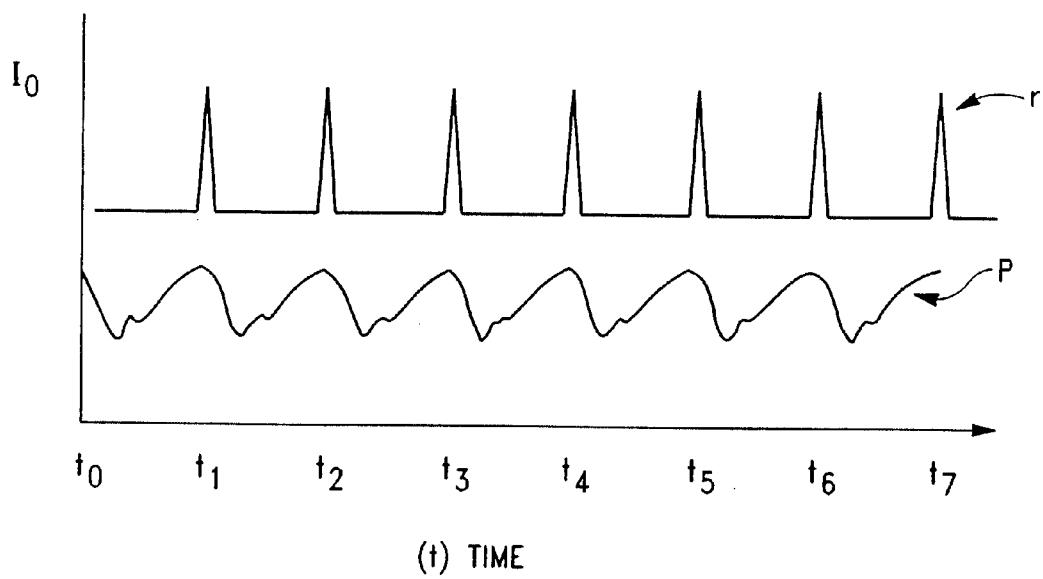
FIG. 8 is a graphical illustration of a reconstructed plethysmographic waveform provided by the first processing means according to the invention.

Referring now to FIG. 8, there is shown a graphical illustration of an "r-wave" portion or component of an electrocardiogram (ECG) waveform (designated r) and the related plethysmographic waveform (designated p). As will be appreciated by one having ordinary skill in the art, the ECG waveform comprises a complex waveform having several components that correspond to electrical heart activity. The QRS component relates to ventricular heart contraction.

The r-wave portion of the QRS component is typically the steepest wave therein, having the largest amplitude and slope, and may be used for indicating the onset of cardiovascular activity. The arterial blood pulse flows mechanically and its appearance in any part of the body typically follows the r wave of the electrical heart activity by a determinable period of time that remains essentially constant for a given patient. See, e.g., Goodlin et al., *Systolic Time Intervals in the Fetus and Neonate,* Obstetrics and Gynecology, Vol. 39, No. 2, (February 1972) and U.S. Pat. No. 3,734,086.

Correlating the occurrence of cardiovascular activity with the detection of arterial pulses typically occurs by measuring an ECG signal, detecting the occurrence of the r-wave portion of the ECG signal, determining the time delay by which an optical pulse in the detected optical signal follows the r-wave, and using the determined time delay between an r-wave and the following optical pulse to evaluate the waveform.

As discussed in detail below, in the present invention, the time delay between successive r-waves is employed to determine and assess the associated plethysmographic waveform. The individualized plethysmographic waveform is then employed as a reference in the correlation canceler to provide a more reliable measurement of oxygen saturation.

Figure 2:
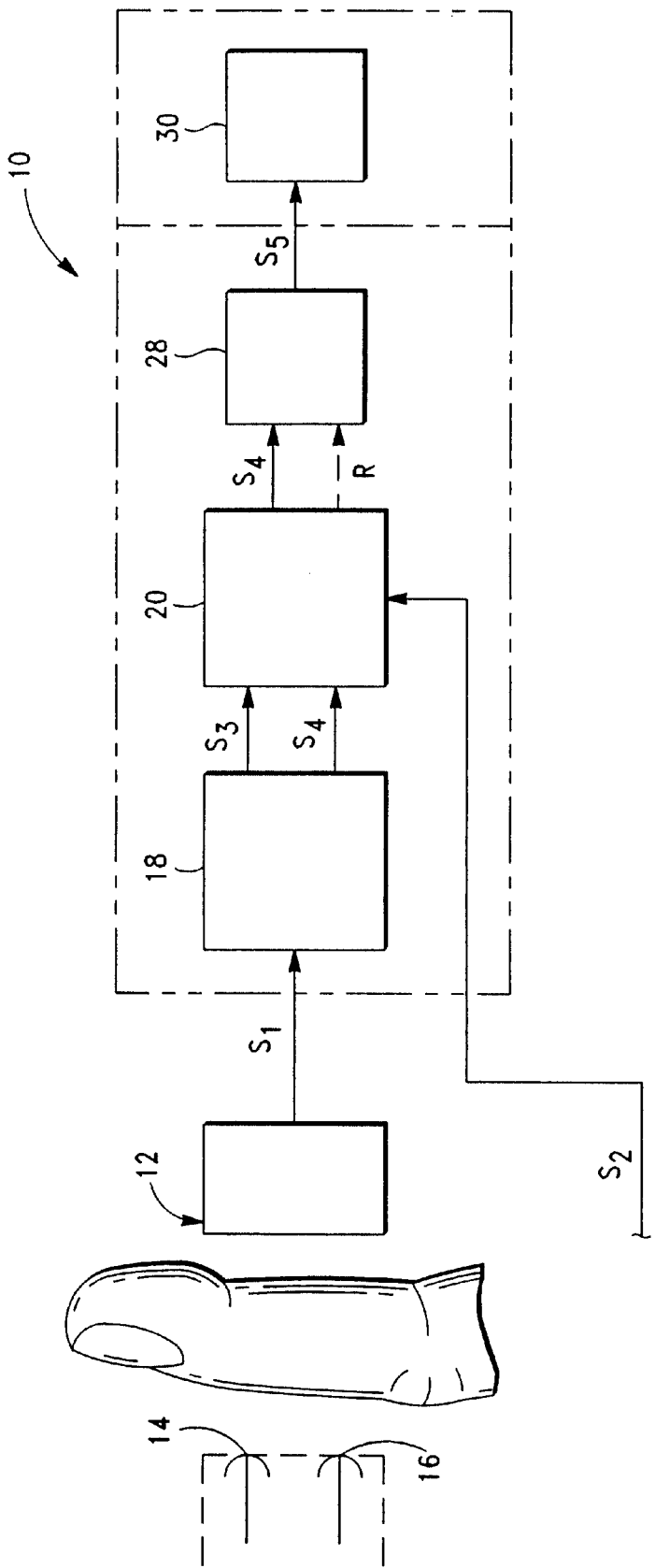
FIG. 2 is schematic illustration of one embodiment of the apparatus for determining blood saturation levels according to the invention.

Referring now to FIG. 2, there is shown a schematic illustration of the method and apparatus (designated generally 10) of the invention. According to the invention, two light emitting diodes (LED's), one LED 14 having a discrete frequency in the range of approximately 650–670 nanometers in the red light range and the other LED 16 having a discrete frequency in the range of approximately 800–1000 nanometers in the infrared range, direct incident light through the finger 5. The light is then detected by a photo detector 12.

The photo detector 12 provides a first output signal $S_1$ that is communicated to a synchronous demodulator 18. As will be appreciated by one having skill in the art, the output signal $S_1$ would be a time multiplexed signal comprising (i) a background signal, (ii) the red light range signal and (iii) the infrared light signal.

The synchronous demodulator 18, which is employed in most pulse oximeter systems, is adapted to remove any common mode signals present and split the time multiplexed signal ($S_1$) into two (2) channels, one representing the red voltage signals (designated $S_3$) and the other representing the infrared voltage signals (designated $S_4$).

Further details of the noted, conventional pulse oximeter components, and related functions, are set forth in U.S. Pat. No. 4,934,372, which is incorporated by reference herein.

As illustrated in FIG. 2, the red and infrared signals $S_3$, $S_4$, and a third signal $S_2$, are communicated to the novel data acquisition device 20. According to the invention, the signal $S_2$ represents an ECG (i.e., electrical potential) signal from the patient 6 preferably acquired during a time period in the range of approximately 2 to 10 sec. (see FIG. 3)

Figure 3:
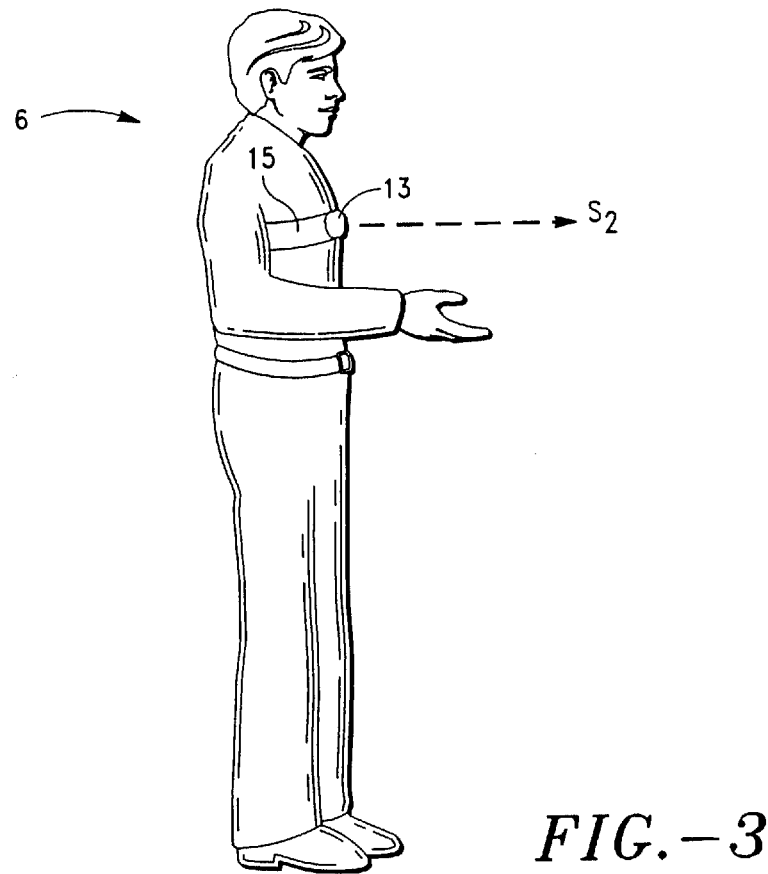
FIG. 3 is a schematic illustration of the ECG monitor according to the invention.

As will be appreciated by one having ordinary skill in the art, the ECG signal can be provided by numerous conventional "hard wired" and "wireless" ECG monitors. As illustrated in FIG. 3, in a preferred embodiment of the invention, the ECG signal $S_2$ is provided by a wireless ECG "r-wave" detector and monitor 13.

In a preferred embodiment of the invention, the ECG detector 13 includes a plurality of quick release snaps (not shown) adapted to removeably engage a torso strap or belt 15, which is preferably positioned proximate the chest cavity. The snaps are further adapted to activate the detector 13 when engaged to the belt 15 and disconnect the detector when disengaged therefrom.

According to the invention, the ECG detector 13 further includes RF transmitter means to provide the ECG signal (i.e., R-wave events) $S_2$ and the data acquisition device 20 includes receiver means adapted to receive the signal $S_2$ (and signals $S_3$ and $S_4$). The ECG signal $S_2$ would, accordingly, be embodied in the RF transmission.

Further details of "hard wired" and "wireless" ECG monitor systems are set forth in U.S. Pat. Nos. 6,026,335; 5,913,827; 5,984,954; 5,876,350; 5,687,717, which are incorporated by reference herein.

Figure 4:
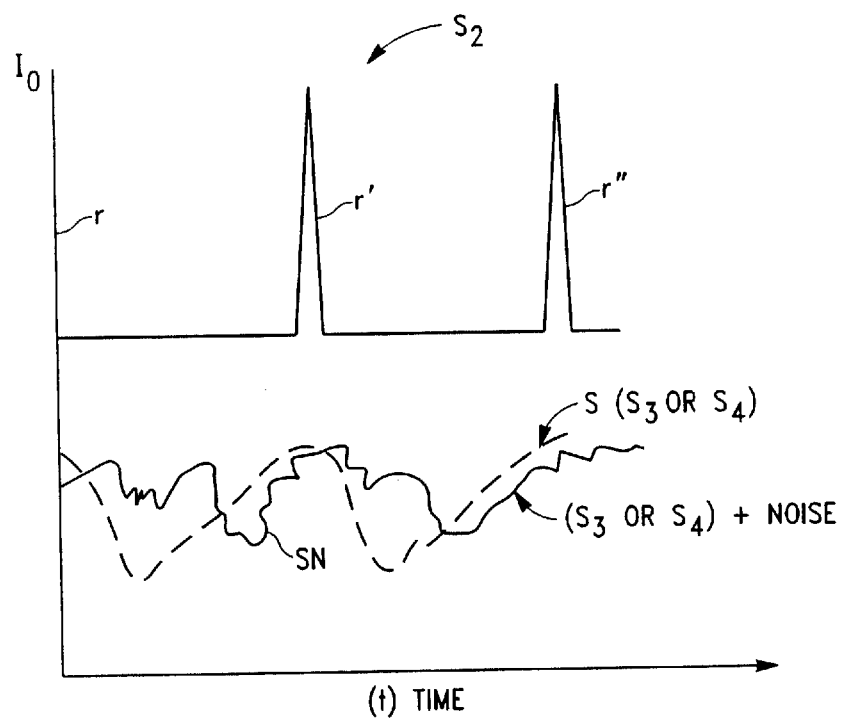
FIG. 4 is a graphical illustration of the red light and infrared light, and r-wave event signals.

Referring now to FIG. 4, there is shown a graphical illustration of the signals $S_2$, $S_3$, $S_4$. As discussed in detail below, the primary component of the ECG signal $S_2$ that is employed in the invention is the time related "r-wave" event; each event designated r, r', r". The red and infrared signals $S_3$, $S_4$ include the base red and infrared voltage signals (which are illustrated by curve S) and, as discussed above, motion artifacts or noise (curve SN).

As indicated, in a preferred embodiment of the invention, the signals $S_2$, $S_3$ and $S_4$ are communicated to the data acquisition device 20. According to the invention, the data acquisition device 20 includes first processing means that is responsive to the ECG signal (i.e., r-wave event) $S_2$. The data acquisition device 20 also provides an accurate representation of the plethysmographic waveform of the patient, including the "quasi-stationary" region of the plethysmographic waveform, referred to hereinafter as the "quasi-stationary heartbeat space."

Figure 5:
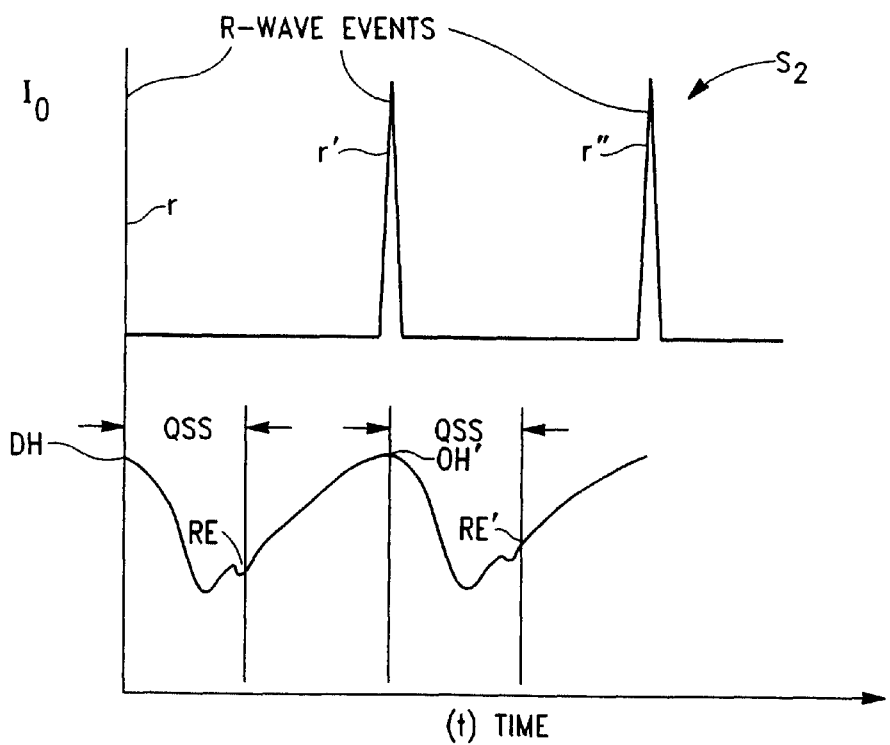
FIG. 5 is a graphical illustration of a plethysmographic waveform, illustrating the quasi-stationary heartbeat spaces or region according to the invention.

Referring to FIG. 5, the "quasi-stationary heartbeat space" (designated QSS), as used herein, is meant to mean the phase within successive heartbeats (i.e., r, r', r") commencing at the point of depolarization of the heart (DH, DH') through commencement of the re-expansion of the heart (RE, RE'), which is proximate the closure of the aortic valve.

Figure 6A:
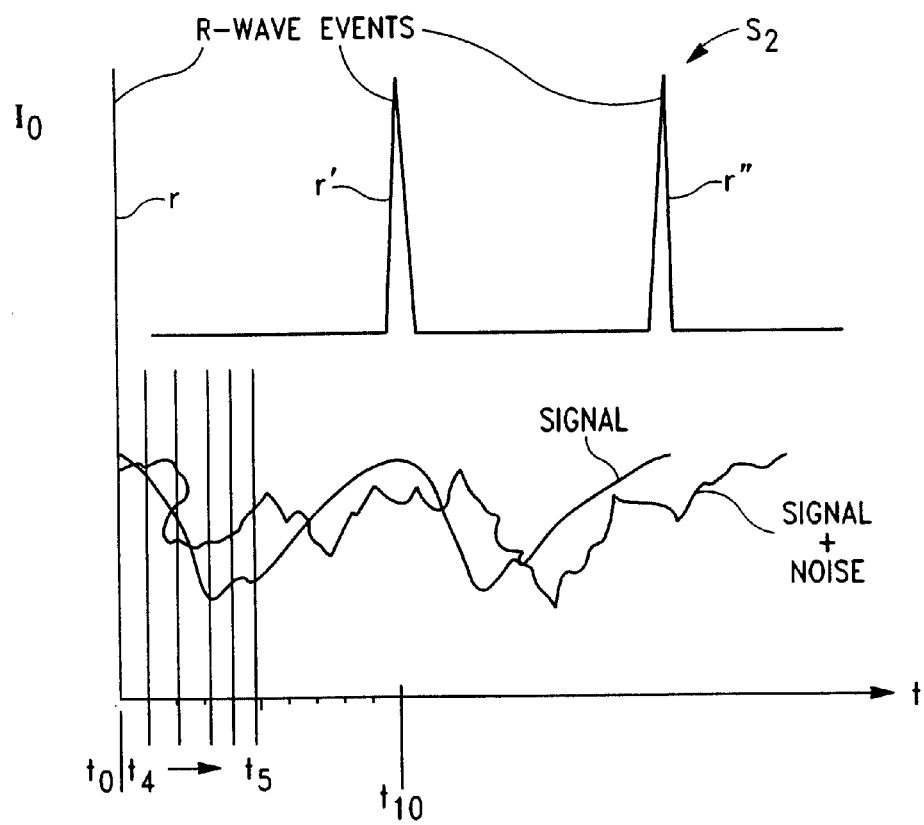
FIG. 6A is a graphical illustration of further r-wave and plethysmographic waveform signals.
Figure 6B:
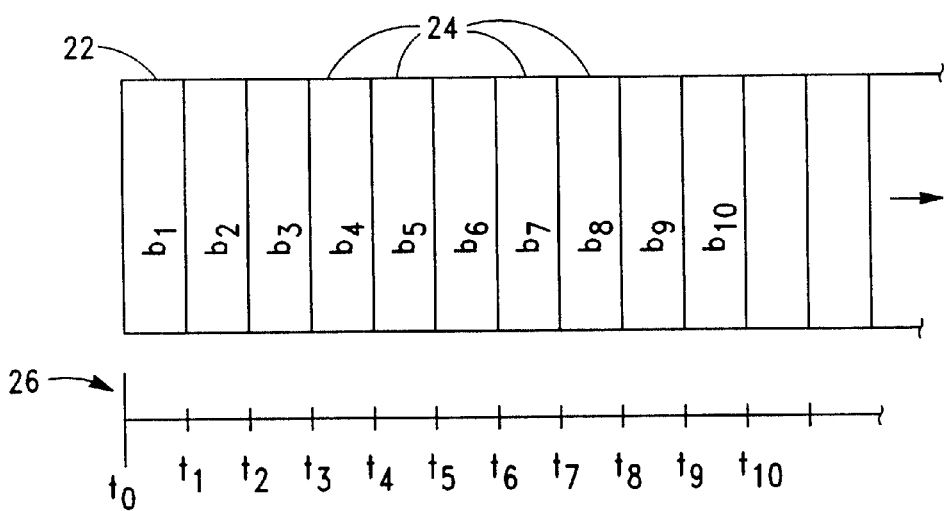
FIG. 6B is a schematic illustration of the first processing means reconstruction buffer and counter according to the invention.

In one embodiment of the invention, the first processing means of the data acquisition device 20 comprises a "synchronous averaging" technique. In this embodiment, the processing means would further include a reconstruction buffer 22 having a plurality of buckets 24 and a counter 26 (see FIG. 6B).

By way of example, assuming the buckets 24 are spaced in time intervals (i.e., $t_1$, $t_2$, $t_3$, etc.) of 20 msec and the time interval (or delay) between r-wave events r and r' (i.e., $t_0$–$t_{10}$) is approximately 1000 msec, the counter 26 would indicate where the signal (or waveform sample) measured at time interval $t_0$–$t_1$ would be placed (i.e., bucket $b_1$). If the sample is extracted during the next time interval (i.e., $t_1$–$t_2$), the sample would be placed in the second bucket $b_2$. The noted process would continue through discrete time intervals of signal sampling between successive r-wave events (i.e., r, r', r").

As will be appreciated by one having ordinary skill in the art, the "synchronous averaging" technique provides a reconstructed waveform the physiologically occurs in time intervals that are representative of the real data. Further details of the "synchronous averaging" technique are set forth in U.S. Pat. No. 4,934,372, which, as indicated above, is incorporated by reference herein.

In an additional embodiment of the invention, the first processing means of the data acquisition device 20 comprises a "binomial averaging" technique. In this embodiment, the buffer 22 and counter 26, discussed above, are also employed.

The data provided to each bucket 26 is, however, different. Generally, in the "binomial averaging" technique the average of the samples (or data points) extracted from the waveform (i.e., signal+noise curve) and placed in respective buckets (i.e., $b_1$, $b_2$, etc.) is initially determined. The average value is then employed as a threshold value (DC). If the data point is >DC, then the data point is assigned a value of +1. If the data point is <DC, then the data point is assigned a value of 0. The noted process similarly continues through discrete signal time intervals of signal sampling during the period between successive r-wave events (i.e., r, r', r").

As will be appreciated by one having ordinary skill in the art, the "binomial averaging" technique similarly provides a reconstructed waveform that is substantially devoid of extraneous data (i.e., motion artifacts). Further details of the "binomial averaging" technique are set forth in U.S. Pat. No. 4,275,744, which is incorporated by reference herein.

Figure 7:
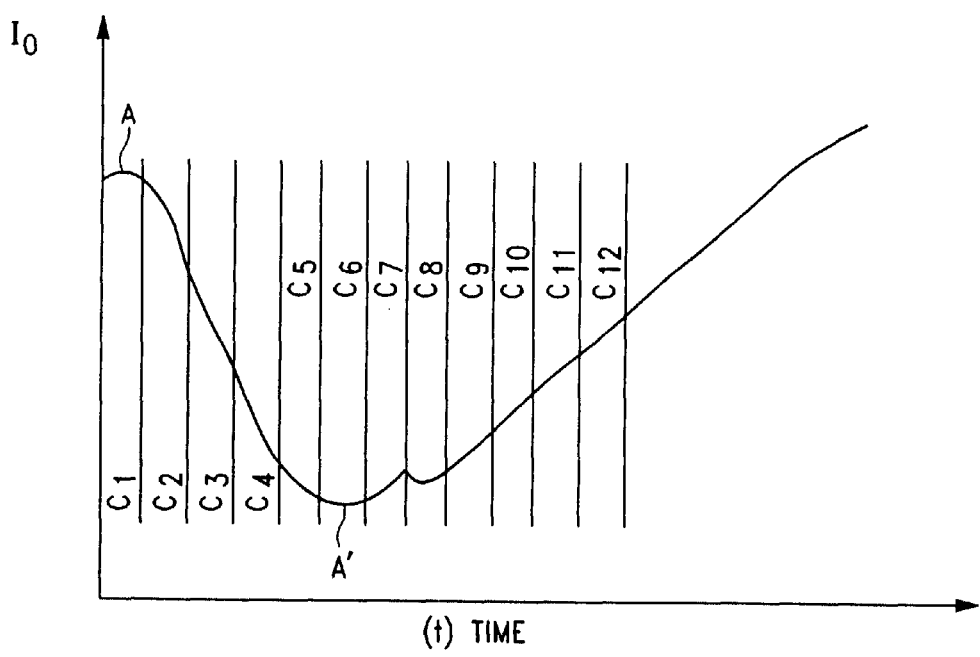
FIG. 7 is a graphical illustration of a further plethysmographic waveform.

In yet another embodiment of the invention, the first processing means of the data acquisition device 20 comprises a "ranked order averaging" technique. As illustrated in FIG. 7, in this embodiment a plurality of equally spaced cells ($C_1$ though $C_{12}$) corresponding to discrete time segments of the waveform are employed.

According to the invention, each sample or data point extracted over the corresponding time segment is ranked, i.e., largest data point A=100, smallest data point A'=0, and the remaining data points ranked with a relative amplitude therebetween.

As will be appreciated by one having ordinary skill in the art, the "ranked order averaging" technique similarly provides a reconstructed waveform that is substantially devoid of extraneous data. Further details of the "ranked order averaging" technique are set forth in the paper entitled *A New Non-Parametric Response-Detection Method,* by Dr. Roger Marsh, presented at the "International Conference on Hearing Screening, Diagnosis and Management of Hearing-Impaired Children," Iowa City, Iowa (Jun. 15, 1996), which is incorporated by reference herein.

Referring now to FIG. 8, there is shown a graphical illustration of the reconstructed plethysmographic waveform (p) provided by the first processing means of data acquisition device 20. As will be appreciated by one having ordinary skill in the art, the plethysmographic waveform illustrated in FIG. 8 is an ideal waveform having substantially equal time intervals (or delays) between r-wave events (i.e., heartbeats). However, in many instances, this is not an accurate representation of a patient's cardiovascular activity. Indeed, rarely does a patient exhibit substantially equal time intervals between heartbeats.

Applicant's have, however, found that, although the time span between heartbeats can vary significantly from heartbeat to heartbeat depending on the state of the patient, there is little, if any, variation in the "quasi-stationary heartbeat space." Thus, as discussed below, in a preferred embodiment of the invention, the "quasi-stationary heartbeat space" is employed as the primary component by the data acquisition device 20 to provide a true, "individualized" plethysmographic waveform.

Figure 9:
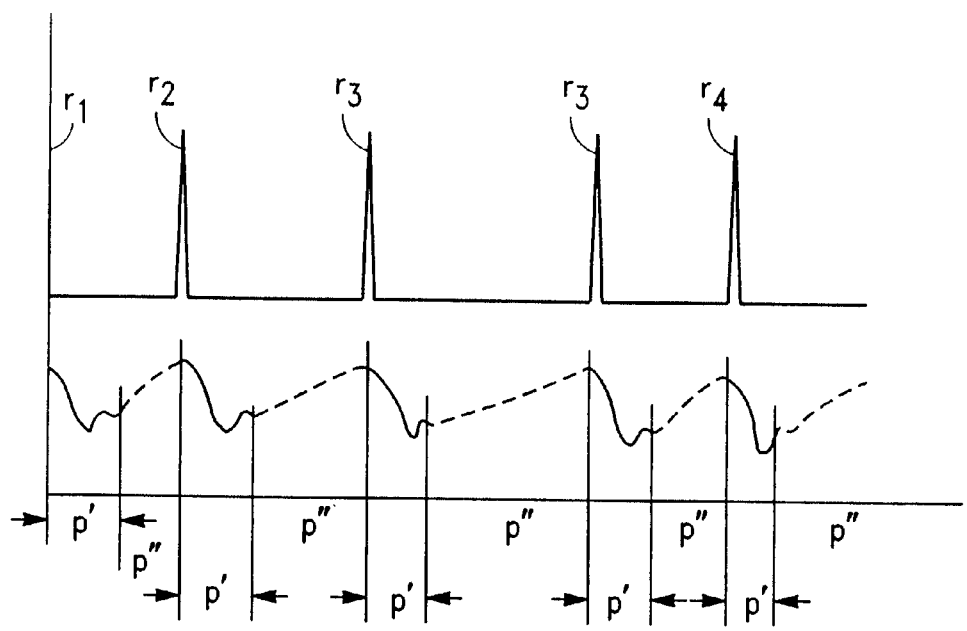
FIG. 9 is a graphical illustration of an individualized plethysmographic waveform provided by the second processing means according to the invention.

According to the invention, the data acquisition device 20 further includes a reference buffer or memory means to store the patient's cardiovascular data (e.g., r-wave pattern or history) and second processing means, which is similarly responsive to r-wave events. Referring now to FIG. 9, in a preferred embodiment of the invention, upon receipt of a first r-wave signal $r_1$ by the buffer, the "quasi-stationary heartbeat space" of the plethysmographic waveform is employed to reconstruct the first time segment (denoted P) of the "individualized" waveform.

A linear extrapolation (or translation) technique is then employed to provide the second (variable) time segment (denoted P") through and until the next r-wave event (i.e., $r_2$) and process repeats itself. As illustrated in FIG. 9, the data acquisition device 20 thus provides a substantially accurate "individualized" plethysmographic waveform for the patient 6.

Referring back to FIG. 2, in a preferred embodiment, the "individualized" plethysmographic waveform is then employed as reference (designated R) that is communicated to and employed by a correlation canceler 28. The infrared signal $S_4$ is also preferably communicated to and employed by a correlation canceler 28, which processes the signals R, $S_4$ in the manner set forth above. The output signal from the correlation canceler 28 (denoted $S_5$) would thus reflect a plethysmographic waveform indication of the true blood oxygen saturation value ($S_pO_2$) of the patient 6.

As will be appreciated by one having ordinary skill in the art, the infrared signal $S_4$ is preferably communicated to the correlation canceler 28 since the infrared signal $S_4$ would have a higher signal-to-noise ratio compared to the red signal $S_3$. However, in additional embodiments of the invention, not shown, two correlation cancelers are employed. In the noted embodiments, the red signal $S_3$ is communicated to the first correlation canceler and the infrared signal $S_4$ is communicated to the second correlation canceler.

According to the invention, the output from the first correlation canceler $\omega_1$ would represent the relative amplitude of the red signal $S_3$. Similarly, the output from the second correlation canceler $\omega_2$ would reflect a relevant amplitude of the infrared signal $S_4$.

The outputs $\omega_1$ and $\omega_2$ from the correlation cancelers are then communicated to computation means. According to the invention, the computation means includes third processing means for determining the correlation ratio of $\omega_1$ and $\omega_2$, which, as will be appreciated by one having ordinary skill in the art, is similarly indicative of the $S_pO_2$ value for the patient.

As illustrated in FIG. 2, in a preferred embodiment of the invention, the signal $S_5$ provided by the correlation canceler 28 (or the signal provided by the computation means discussed above) is communicated to conventional display means 30 to display the $S_pO_2$ value for the patient 6. The display means 30 can also display other pertinent information relating to the patient, separately or in conjunction with the $S_pO_2$ value(s), and/or provide one or more audio warning signals at preset $S_pO_2$ threshold values.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A method for determining blood oxygen saturation level of a patient's blood, comprising the steps of:

acquiring a first blood oxygen signal from the patient;

acquiring an additional physiological signal having a heart rate component, said second acquiring step using an acquisition technique that is different and independent from said first acquiring step;

processing said first blood oxygen signal and said physiological signal to provide a first waveform signal;

processing said first waveform and said physiological signal to provide a reference waveform; and processing said reference waveform and said first blood oxygen signal to provide a second blood oxygen signal corresponding to the blood oxygen saturation level of said patient, said reference waveform and first blood oxygen signal processing being performed with correlation canceling.

2. The method of claim 1, wherein said first waveform includes a plurality of quasi-stationary heartbeat spaces.

3. The method of claim 2, wherein said heart rate component comprises plurality of first r-wave signals corresponding to first r-wave events.

4. The method of claim 3, wherein said reference waveform includes said plurality of quasi-stationary heartbeat spaces and a plurality of second r-wave events substantially corresponding to said first r-wave events.

5. The method of claim 1, wherein:
said first acquiring step acquires red and infrared pulse oximetry signals; and
said second acquiring step acquires electrocardiogram signals.

6. The method of claim 1, wherein said first processing step comprises synchronous averaging.

7. The method of claim 1, wherein said first processing step comprises binomial averaging.

8. The method of claim 1, wherein said first processing step comprises ranked order averaging.

9. A method for determining blood oxygen saturation level of a patient's blood, the patient having a tissue region and a heart, the heart having an electrical potential, comprising;
passing first and second lights through said patient's tissue region, said first light being substantially in a red light range and said second light being substantially in an infrared light range;
detecting the light absorbed by said tissue region and providing a first signal corresponding to said absorbed light;
processing said first signal to provide a second signal corresponding to at least one red light signal component and a third signal corresponding to at least one infrared light signal component;
detecting said heart electrical potential and providing an ECG signal corresponding to said heart electrical potential, said ECG signal including a plurality of first r-wave components corresponding to first r-wave events;
processing said first, second and ECG signals to provide a first waveform, said first waveform including a plurality of quasi-stationary heartbeat spaces;
processing said first waveform and said ECG signal to provide a second waveform, said second waveform including said plurality of quasi-stationary heartbeat spaces and a plurality of second r-wave events substantially corresponding to said first r-wave events; and
processing said third signal and said second waveform to provide a fourth signal, said fourth signal substantially corresponding to the blood oxygen saturation level of said patient.

10. The method of claim 9, wherein said first processing step comprises synchronous demodulation.

11. The method of claim 9, wherein a wireless ECG monitor is used to detect said electrical potential.

12. The method of claim 9, wherein said first processing step comprises synchronous averaging.

13. The method of claim 9, wherein said first processing step comprises binomial averaging.

14. The method of claim 9, wherein said first processing step comprises ranked order averaging.

15. The method of claim 9, wherein said first processing step comprises correlation canceling.

16. An apparatus for determining blood oxygen saturation level of a patient's blood, comprising:
an oximeter sensor arrangement coupled to said patient for acquiring a first blood oxygen signal;
an ECG detector coupled to said patient for acquiring an ECG signal, said ECG signal including a plurality of first r-wave components substantially corresponding to first r-wave events;
first processing means for processing said first blood oxygen signal and said ECG signal to provide a first waveform, said first waveform including a plurality of quasi-stationary heartbeat spaces;
second processing means for processing said first waveform and said ECG signal to provide a second waveform, said second waveform including said plurality of quasi-stationary heartbeat spaces and a plurality of second r-wave events substantially corresponding to said first r-wave events; and
third processing means for processing said first blood oxygen signal and said second waveform, said third processing means being adapted to provide a second blood oxygen signal substantially corresponding to the blood oxygen saturation level of said patient.

17. The apparatus of claim 16, wherein said third processing means comprises a correlation canceler.

18. The apparatus of claim 16, wherein said apparatus includes memory means adapted to record said first and second blood oxygen signals, said ECG signal and said first and second waveforms.

19. An apparatus for determining blood oxygen saturation level of a patient's blood, the patient having a tissue region and a heart, the heart having an electrical potential, comprising;
a plurality of light means for passing first and second lights through said subject's tissue region, said first light being substantially in a red light range and said second light being substantially in an infrared range;
a photo detector adapted to detect the light absorbed by said tissue region, said photo detector being further adapted to provide at least a first signal corresponding to said absorbed light;
a demodulator in communication with said photo detector, said demodulator being adapted to provide a second signal corresponding to at least one red light signal and a third signal corresponding to at least one infrared signal in response to said first signal;
an ECG detector adapted to detect the electrical potential generated by said patient's heart, said ECG detector being further adapted to provide an ECG signal corresponding to said electrical potential, said ECG signal including a plurality of first r-wave components corresponding to first r-wave events;
a data acquisition device in communication with said demodulator and ECG detector, said data acquisition device including first processing means for processing said second, third and ECG signals to provide a first waveform, said first waveform including a plurality of quasi-stationary heartbeat spaces, and second processing means for processing said first waveform and said ECG signal to provide a second waveform, said second waveform including said plurality of quasi-stationary heartbeat spaces and a plurality of second r-wave events substantially corresponding to said first r-wave events; and
correlation canceler for processing said second waveform and said third signal to provide a $S_pO_2$ signal, said $S_pO_2$ signal substantially corresponding to the blood oxygen saturation level of said patient.

* * * * *